United States Patent
Tatarchuk et al.

(10) Patent No.: US 10,543,470 B2
(45) Date of Patent: Jan. 28, 2020

(54) REACTORS AND METHODS FOR PROCESSES INVOLVING PARTIAL OXIDATION REACTIONS

(71) Applicants: IntraMicron, Inc., Auburn, GA (US); Auburn University, Auburn, AL (US)

(72) Inventors: Bruce Tatarchuk, Auburn, AL (US); David Scarborough, Lafayette, AL (US); Paul Dimick, Auburn, AL (US); Hongyun Yang, Auburn, AL (US)

(73) Assignees: IntraMicron, Inc., Auburn, AL (US); Auburn University, Auburn, AL (US)

(*) Notice: Subject to any disclaimer, the term of this patent is extended or adjusted under 35 U.S.C. 154(b) by 0 days.

(21) Appl. No.: 15/967,078

(22) Filed: Apr. 30, 2018

(65) Prior Publication Data

US 2018/0311631 A1 Nov. 1, 2018

Related U.S. Application Data

(60) Provisional application No. 62/491,928, filed on Apr. 28, 2017.

(51) Int. Cl.

| B01J 8/34 | (2006.01) |
|---|---|
| B01J 8/00 | (2006.01) |
| B01J 4/00 | (2006.01) |
| B01J 8/02 | (2006.01) |
| C07B 41/04 | (2006.01) |
| C07B 43/08 | (2006.01) |
| C07D 301/08 | (2006.01) |
| C07B 41/06 | (2006.01) |

(52) U.S. Cl.
CPC ............... B01J 8/34 (2013.01); B01J 4/001 (2013.01); B01J 8/008 (2013.01); B01J 8/0242 (2013.01); B01J 8/0278 (2013.01); B01J 8/0285 (2013.01); B01J 2208/00017 (2013.01); B01J 2219/0018 (2013.01); B01J 2219/00265 (2013.01); C07B 41/04 (2013.01); C07B 41/06 (2013.01); C07B 43/08 (2013.01); C07D 301/08 (2013.01)

(58) Field of Classification Search
CPC ..... B01J 4/001; B01J 8/34; B01J 8/008; B01J 8/0242; B01J 8/0278; B01J 8/0285
USPC .......................................................... 422/129
See application file for complete search history.

(56) References Cited

U.S. PATENT DOCUMENTS

| 4,585,798 A | 4/1986 | Beuther |
| 5,036,032 A | 7/1991 | Iglesia |
| 5,733,839 A | 3/1998 | Espinoza |
| 5,849,254 A * | 12/1998 | Suzuki ................. B01D 53/945 423/213.5 |
| 6,075,062 A | 6/2000 | Zennaro |
| 6,136,868 A | 10/2000 | Culross |
| 6,262,131 B1 | 7/2001 | Arcuri |
| 6,353,035 B2 | 3/2002 | Manzer |
| 6,368,997 B2 | 4/2002 | Herron |

(Continued)

*Primary Examiner* — Huy Tram Nugyen
(74) *Attorney, Agent, or Firm* — Pabst Patent Group LLP

(57) ABSTRACT

Described herein are improved chemical reactors for carrying out partial oxidation reactions. The chemical reactor permits the use of levels of oxygen above the lower explosion limit (LEL) typically used in partial oxidation reactions, which increases both volumetric reactivity and conversion per pass, resulting in reduced separation and reactant recycle costs. Also described are methods of using the reactors.

25 Claims, 1 Drawing Sheet

(56) References Cited

U.S. PATENT DOCUMENTS

| | | | |
|---|---|---|---|
| 6,451,864 B1 * | 9/2002 | Wang | B01J 8/0285 |
| | | | 518/715 |
| 6,476,085 B2 | 11/2002 | Manzer | |
| 6,490,880 B1 | 12/2002 | Walsh | |
| 6,537,945 B2 | 3/2003 | Singleton | |
| 6,558,634 B1 | 5/2003 | Wang | |
| 7,084,180 B2 | 8/2006 | Wang | |
| 8,314,044 B2 * | 11/2012 | Jangbarwala | B01J 21/18 |
| | | | 428/293.4 |
| 8,420,023 B2 * | 4/2013 | Tatarchuk | B01J 19/2405 |
| | | | 422/198 |
| 8,444,939 B2 | 5/2013 | Bowe | |
| 8,946,111 B2 * | 2/2015 | Jangbarwala | B01J 37/08 |
| | | | 428/293.4 |
| 9,359,271 B2 | 6/2016 | Leviness | |
| 2002/0004450 A1 * | 1/2002 | Gaffney | B01J 23/464 |
| | | | 502/256 |
| 2002/0028853 A1 | 3/2002 | Manzer | |
| 2002/0188031 A1 | 12/2002 | Kibby | |
| 2003/0105171 A1 | 6/2003 | Subramanian | |
| 2013/0259767 A1 * | 10/2013 | Whittenberger | B01J 8/008 |
| | | | 422/198 |
| 2015/0073184 A1 * | 3/2015 | Caciula | C07C 5/48 |
| | | | 585/254 |

* cited by examiner

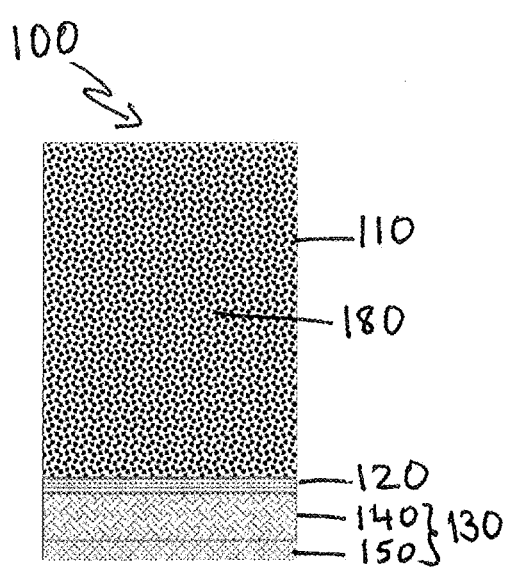
Figure 1A
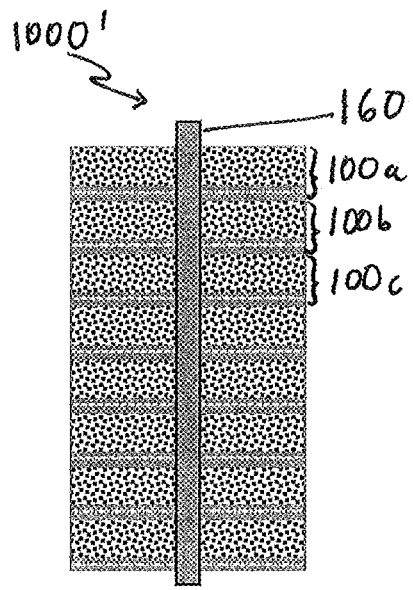
Figure 1B
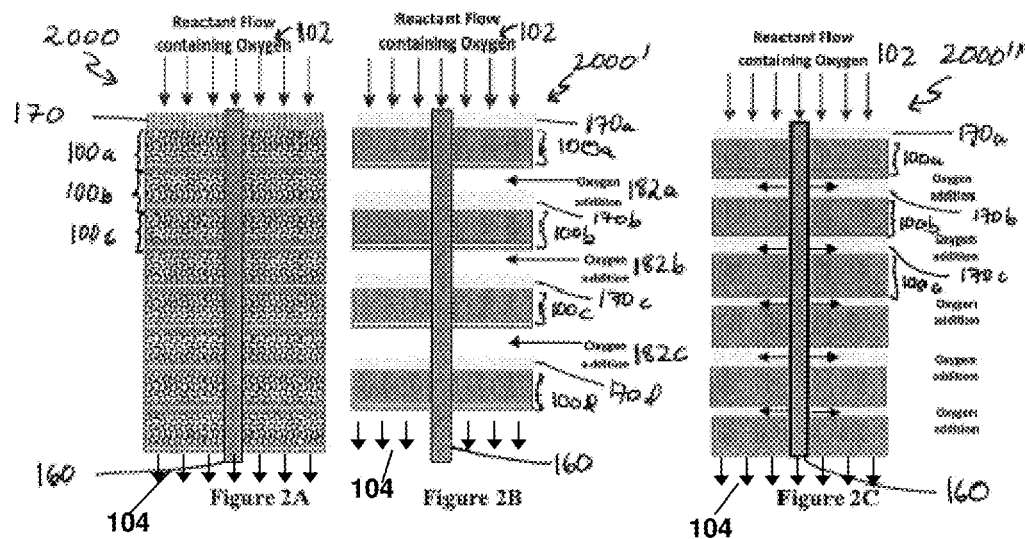

REACTORS AND METHODS FOR PROCESSES INVOLVING PARTIAL OXIDATION REACTIONS

CROSS-REFERENCE TO RELATED APPLICATION

This application claims benefit of and priority to U.S. Application No. 62/491,928 filed on Apr. 28, 2017, the disclosure of which is incorporated herein in its entirety.

FIELD OF THE INVENTION

This invention is generally in the field of chemical reactors, in particular chemical reactors for performing exothermic reactions, such as partial oxidation reactions.

BACKGROUND OF THE INVENTION

Partial oxidation reactions are important in the production of a variety of chemicals and fuels. These reactions are typically highly exothermic and often have significant adiabatic temperature rises. Further these reactions often generate free radicals. The selectivity of these reactions is very sensitive to temperature, such that reactors undergoing excessive reaction develop hot spots that lead to reactant ignition and/or a product selectivity that shifts toward total oxidation.

To address these problems, reactors are commonly designed or operated: (i) using small diameter reactor tubes with high surface to volume ratios for higher heat transfer rates, (ii) by reducing the reaction rate per unit volume inside the tubular reactor, such as by placing inert material into catalyst beds, (iii) using sub-stoichiometric levels of oxygen to limit the extent of reaction, (iv) by introducing inert gases to the reactant fluid to serve as a thermal sink for the exothermicity of the reaction, and/or (v) by introducing inert gases to dilute combustible gas concentration to below the explosion threshold. These approaches are used to lower the rate of reaction per unit volume, in order to maintain the temperature inside the reactor tube within a desired range. However, these approaches also increase inefficiencies in reactors, such as low reactant per pass conversion, and/or high cost and energy requirements.

Therefore, there is a need for safer and/or more efficient reactors.

SUMMARY OF THE INVENTION

Described herein, is a more efficient reactor for that is configured to prevent the development and/or propagation of a fire in the reactor for partial oxidation reactions. Also described are methods of making and using the reactor.

The reactor contains a vessel, and a process channel having an inner wall. The process channel is located within the vessel. The process channel contains a composite catalyst structure that includes a catalyst layer, and optionally a barrier layer, a heat spreader layer, or both. The heat spreader layer can include a quenching layer, a flame blocking layer, or both. Preferably, a catalyst is not present in the barrier layer and/or heat spreader layer. An exothermic reaction, such as a partial oxidation reaction, occurs within the catalyst layer leading to the formation of free radicals. The catalyst layer has a suitable thickness, such that the temperature of the fluid at the outlet of the catalyst layer is below the safety threshold for propagating a fire or causing an explosion. The catalyst layer itself can also function as a flame retardant or flame arrestor especially when the process exothermicity is not very strong. Processes that have sufficiently low process exothermicity for the catalyst layer to function as the flame retardant or flame arrestor typically have a reaction heat of less than 50 kJ/mol of carbon. An example of such a process is the water-gas shift (WGS), which has a heat of reaction of 41 kJ/mol. Thus, in some embodiments, the composite structure contains a catalyst layer that functions as a flame retardant or flame arrestor, optionally the composite structure does not contain an additional layer that functions as a flame retardant or flame arrestor.

The process channel in the reactor can contains a stack of two or more composite catalyst structures, where each composite catalyst structure may be the same or different.

Preferably, the catalyst layer contains a micro-structured catalyst carrier or support that has high thermal conductivity to transfer heat from the channel to the inside wall of the process channel. Additionally, the catalyst layer may have a suitable structure to reduce or prevent the formation of intrabed hot spots, which can lead to reactant ignition, and poor selectivity to partial oxidation products.

High thermal conduction further allows non-diluted and more active catalysts to be used in large process channels, such as 4-inch process channels for extremely high exothermic reactions, e.g. Fischer Tropsch synthesis. The micro-structured catalyst carrier or support can include internal pores or openings having sizes ranging from between about 1 micron and 100 microns, inclusive. The internal domain size of the catalyst carrier or support may be suitable to prevent any free radicals produced within the process channel from propagating a flame or explosion, because they are rapidly quenched by wall collisions on the cold surface of the micro-structures.

The barrier layer keeps the catalyst from migrating out of the catalyst layer.

Generally, the heat spreader layer collects heat from a reactive fluid stream and dissipates the heat to the process channel's wall, where it is removed. Further, the heat spreader layer quenches free radicals, by virtue of the quenching layer that quenches free radicals produced in the catalyst layer. Quenching the free radicals is generally effective to prevent the propagation of a fire or explosion.

The reactor is configured to safely permit levels of reactants above the standard lower explosion limit (LEL) or above the thresholds for oxygen content to be used in a given exothermic reaction. This increases both volumetric reactivity and per pass conversion, resulting in a reactor with reduced operation costs and greater efficiency. Additionally, the reactors and methods of use described herein increase safety compared to reactors without the ability to quench free radicals and/or prevent an explosion or the propagation of a fire.

This improved efficiency per pound of product produced also provides a reduction in global greenhouse gas emissions.

BRIEF DESCRIPTION OF THE DRAWINGS

FIG. 1A is a schematic showing different layers of an exemplary composite catalyst structure. FIG. 1B is a schematic cross-sectional view of an exemplary reactor, where the reactor includes of a stack of a plurality of composite catalyst structures.

FIGS. 2A, 2B, and 2C are schematics of exemplary reactors containing a stack of composite catalyst structures having a mechanical support structure (e.g., a rod) and a flow distribution layer at the top of the stacked composite catalyst structures. Oxygen is added before a reactant fluid (gas stream) reaches the catalyst layer. In FIG. 2B, extra oxygen is added from one or more additional oxygen feeds, located along the length of the process channel. As shown, optionally, the reactor includes a gap separating successive composite catalyst structures and the flow distribution layers. In FIG. 2C, extra oxygen is added through the mechanical support structure and diffuses into one or more flow distribution layers inside the process channel containing the stack of more than one composite catalyst structures. As shown, the composite catalyst structures and flow distribution layers optionally abut each other.

DETAILED DESCRIPTION OF THE INVENTION

I. Definitions

"Flame retardant" and "flame arrestor" are used interchangeably, and mean a material that impedes the propagation of a flame.

"Process channel" refers to a channel in which a chemical transition of one molecule into another molecule or product occurs, under certain conditions of temperature and pressure.

"Reactant fluid" and "Reactant flow" refer to a fluid that contains a molecule that can undergo a chemical transformation into another molecule or product at the temperature and pressure conditions within a process channel.

II. Reactors

The chemical reactors described herein contain a vessel and a process channel having an inner wall. The process channel is inside the vessel. One or more chemical reactions occur inside the process channel. The chemical reactions can be partial oxidative reactions in the presence of oxygen. In some reactions operated at high temperatures, free radical species can be generated. The reactor is configured to operate at a temperature that is greater than 200° C. but less than 1000° C., such as between 200° C. to 950° C., inclusive, between 300° C. and 950° C., inclusive, between 400° C. to 950° C., inclusive, between 400° C. to 800° C., inclusive, between 200° C. to 550° C., inclusive, between 250° C. to 900° C., inclusive, or between 300° C. to 800° C., inclusive, and a pressure from ambient (1 atm) to several hundred pounds per square inch gage (psig).

Exemplary reactors are schematically depicted in FIGS. 1B, 2A, 2B, and 2C.

1. Process Channel

Referring to FIG. 1A, the process channel contains a composite catalyst structure 100 that includes a catalyst layer 110. The composite catalyst structure 100 can further include a barrier layer 120, a heat spreader layer 130, or both. The heat spreader layer 130 can include a quenching layer 140, a flame blocking layer 150, or both. Generally, the barrier layer 120 and heat spreader layer 130 do not contain a catalyst. Typically, the composite catalyst structure 100 includes at least a catalyst layer 110 and a barrier layer 120. The catalyst layer may have a thickness that is greater than each of the thicknesses of the barrier layer 120 and the heat spreader layer 130, if present. All layers, except the catalyst layer, may have a thickness of less than 10 mm, preferably less than 5 mm. The layers can be formed from the same or different materials.

Referring to FIG. 1B, in some forms, the process channel within the reactor can contain a stack 1000' containing two or more composite catalyst structures (100a, 100b, 100c, etc) shown in FIG. 1A, and optionally including a mechanical supportive structure 160 to support the stack. The catalyst structure in the stack can be similar to the arrangement of layers shown in FIG. 1A. It is also contemplated that the arrangement of layers within each composite catalyst structure in the stack can be different. Preferably, the top layer in each composite catalyst structure in the stack is the catalyst layer 110. As shown in FIG. 1B, the composite catalyst structures can be stacked, such that successive composite catalyst structures abut each other. In some forms, there is a gap between successive composite catalyst structures (see, e.g. FIG. 2B).

Referring to FIG. 2A, the process channel may contain a stack 2000 which includes the stack 1000' shown in FIG. 1B, and an additional flow distribution layer 170 at the top of the stack of composite catalyst structures (100a, 100b, 100c, etc). In this configuration, a reactant fluid containing oxygen contacts the flow distribution layer before contacting a catalyst layer (or a first catalyst layer) in the stack.

Referring to FIG. 2B, the process channel may contain a stack 2000' with a plurality of composite catalyst structures (100a, 100b, 100c, etc) shown in FIG. 1A stacked on top of each other. As shown in FIG. 2B, each composite catalyst structure has a flow distribution layer 170a abutting at least one catalyst layer 110a, and a gap 182a between successive composite catalyst structures (e.g., between 100a and 100b) and optionally, a further flow distribution layer 170b at the top of each subsequent composite catalyst structure (see, e.g. 100b, 100c, 100d). In addition to having oxygen in the inlet reactant fluid 102, additional oxygen streams can be added to the reactant fluid as it flows through the process channel, from one or more openings, i.e. oxygen side inlets 182a, 182b, 182c, in the wall of the process channel. In some forms, extra oxygen can also be added through the mechanical support structure 160.

Referring to FIG. 2C, in some forms, the process channel contains a stack 2000" with a plurality of composite catalyst structures (100a, 100b, 100c, etc), such as shown in FIG. 1A, stacked on top of each other. Each composite catalyst structure may contain a flow distribution layer 170a abutting at least one catalyst layer 110a. Further, successive composite catalyst structures, which contain a further catalyst layer 110b and optionally a further flow distribution layer 170b, can abut each other. In addition to having oxygen in the inlet reactant fluid 102, extra oxygen streams can be added to the reactant fluid as it flows through the process channel, from one or more openings, i.e. oxygen side inlets 182a, 182b, 182c, in the wall of the process channel. In some forms, extra oxygen can also be added through the mechanical support structure 160.

Each reactor includes at least one reactant flow inlet 102 and at least one product flow outlet 104. Oxygen typically is mixed with the reactant at the inlet. Additionally, oxygen may be added via one or more additional oxygen side inlets (182a, 182b, 182c, etc) as the reactant flows through the process channel.

If needed, if reactants remain in the stream at the outlet, the fluid may be recycled through the process channel (not shown in figure).

In some forms, the process channels have walls that are made from materials that allow heat exchange on their external surfaces. Preferred materials include, but are not limited to metals and metal alloys.

a. Catalyst Layer
i. Materials

Referring to FIG. 1A, the catalyst layer 110 includes a catalyst 180. In some forms, the catalyst can be in particulate form. Suitable catalysts include, but are not limited to, metals such as silver, iron, aluminum, cobalt, copper, chromium, molybdenum, vanadium, bismuth; alloys of these metals; iron oxides; molybdenum oxides; vanadium oxides; and bismuth phosphomolybdate; and combinations thereof.

In some forms, the catalyst layer can include any material that can be used as a catalyst support. The catalyst can be dispersed on and/or within the catalyst support. Suitable catalyst supports include, but are not limited to metals, such as copper, silver, zinc, aluminum, nickel, platinum; alloys of these metals; silica; ceramics; pumice; silica gel; various silicates; aluminosilicates; $SBA\text{-}SiO_2$; ZSM zeolites; alumina; and silicon carbide; metal oxides, such as $\gamma\text{-}Al_2O_3$, $SiO_2$, $ZrO_2$, $TiO_2$, tungsten oxide, magnesium oxide, vanadium oxide, chromium oxide, manganese oxide, iron oxide, nickel oxide, cobalt oxide, copper oxide, zinc oxide, molybdenum oxide, tin oxide, calcium oxide, aluminum oxide, lanthanum series oxide(s), zeolite(s); and combinations thereof.

Preferably, when the catalyst is dispersed on a catalyst support (also referred to as a substrate), the catalyst is in particulate form. Preferably, the catalyst particles on the catalyst support are physically isolated from each other, in order to avoid the creation of hot spots during a chemical reaction. The diameters of the catalyst particles can be between 1 μm and 500 μm, inclusive, between 50 μm and 400 μm, inclusive, between 100 μm and 300 μm, inclusive, or between 100 μm and 200 μm, inclusive.

ii. Properties

The catalyst layer is thin enough, such that the temperature at the outlet of this layer is below the safety threshold for autoignition or causing an explosion. It can be important to have a thin catalyst layer, so that any flame that is generated within the catalyst layer, in some extreme cases, can be quenched by the quenching layer for the protection of downstream catalyst structures. In some forms, the catalyst layer can have a thickness between 0.5 mm and 20 mm, inclusive, between 0.5 mm and 15 mm inclusive, or between 0.5 mm and 10 mm. In some forms the thickness of the catalyst layer is less than 5 mm for extremely high exothermic partial oxidation reactions, such as oxidative coupling of methane within the broad class of oxidative coupling reactions (OCM).

The materials used to form the catalyst layer, can be designed such that the catalyst layer is in the form of a packed bed, microfibrous medium, non-sintered metal mesh, sintered metal mesh, metal foam, wool, metal honeycomb, or metal monolith, or a combination thereof. In some forms, these structural designs within the catalyst layer, can improve heat transfer and avoid hot spot formation in the catalyst layer.

Microfibrous media with catalyst entrapped therein are described for example in U.S. Pat. No. 8,420,023 to Tatarchuk, et al., the disclosure of which is incorporated herein.

The materials that form the catalyst layer can have any thermal conductivity, such as between 10 W/m-K and 400 W/m-K, inclusive, such as between 10 W/m-K and 300 W/m-K, inclusive, 10 W/m-K and 200 W/m-K, inclusive, 10 W/m-K and 100 W/m-K, inclusive, 10 W/m-K and 65 W/m-K, inclusive. Exemplary suitable materials for forming the catalyst layer include copper, aluminum, nickel, and stainless steel. When a microfibrous medium is used, the catalyst can be entrapped within a microfibrous mesh structure made of micron-sized ceramic or metal fibers. Optionally, the microfibrous media are copper microfibrous media (e.g. with a thermal conductivity of about 65 W/m-K) or nickel microfibrous media (e.g. with a thermal conductivity of about 10 W/m-K).

The total solid fraction in the catalyst layer can be between 1% volume and 70% volume, inclusive, preferably between 10% volume and 50% volume, inclusive, most preferably between 20% volume and 40% volume. In some forms the total solid fraction in catalyst layer is about 30% volume. In some forms, the catalyst layer can have a catalyst occupancy of between 1% volume and 50% volume, inclusive, between 1% volume and 40% volume, inclusive, between 1% volume and 30% volume, inclusive, 1% volume and 25% volume, inclusive, 5% volume and 20% volume, inclusive, or 5% volume and 15% volume, inclusive.

In some forms, in addition to catalyzing a chemical reaction, the catalyst layer can also act as a flame retardant or flame arrestor. In these cases, the catalyst layer typically has high thermal conductivities, high interstitial surface area, and small opening size on the gas outlet surface, such that hot spots can be avoided, free radicals can be paired (i.e., quenched), and gas outlet velocities can be higher than the flame speed for the given reactions and conditions.

As a non-limiting example, when the catalyst layer includes a microfibrous medium for immobilizing small particles of catalyst, i.e., microfibrous entrapped catalyst; the catalyst layer can act as a flame retardant, as well as facilitate enhanced heat and mass transfer. The catalyst layer simultaneously carries out the desired reaction and prevents the reaction from generating local hot spots for strongly exothermic reactions in the absence of oxidants (such as oxygen, chlorine, nitrogen oxides, etc.) such as in Fischer-Tropsch synthesis, methanol synthesis, etc., as shown in U.S. Pat. No. 8,420,023 to Tatarchuk, et al. In the presence of oxygen and the strongly exothermic reactions noted above, efficient heat transfer helps to avoid hot spot formation and also special precautions to avoid flame generation.

b. Barrier Layer

The barrier layer 120 prevents the catalyst from migrating out of the catalyst layer (packed bed or microfibrous media bed). The barrier layer 120 can be a microfibrous medium, screen, metal ribbon, metal foam, or a mesh structure, or a combination thereof. Preferably, the interstitial spaces or pore sizes of the materials in the barrier layer are less than those found in the materials within the catalyst layer(s). In some forms, the pore size or interstitial space of the material within the barrier layer is at most half that of the size of the catalyst particles in the catalyst layer 110. When the barrier layer 120 includes fibers, such as in a microfibrous medium, the fibers can have a diameter between 0.5 micron and 50 microns, inclusive, between 1 micron and 40 microns, inclusive, between 1.5 microns and 32 microns, inclusive, between 5 microns and 20 microns, inclusive, preferably between 6 microns and 12 microns, inclusive.

The barrier layer is typically thin, such as with a thickness between 0.1 and 10 mm, inclusive, between 0.1 mm and 5 mm, inclusive, between 1 mm and 5 mm, inclusive, optionally the thickness is between 1 mm and 2 mm, inclusive, or even smaller, such as between 0.1 mm and 1 mm, inclusive, or between 0.1 mm and 0.5 mm, inclusive.

c. Heat Spreader Layer

Referring to FIG. 1A, the heat spreader layer 130 contains a quenching layer 140, a flame blocking layer 150, or both. Preferably, the flame blocking layer 150 has a higher metal volume occupancy, compared to the quenching layer 140. The pore sizes or interstitial spaces of the material(s) in the heat spreader layer 130 may be larger than those of the barrier layer 120, i.e., the heat spreader layer can contain more coarse pores compared to the pores in the barrier layer 120. In some forms, the quenching layer and flame blocking layer are made of the same material, e.g. the same metal. In some forms, the heat spreader layer contains fine metal fibers. In some forms, the heat spreader layer has a thickness between 0.1 and 10 mm, inclusive, or between 0.1 and 5 mm, inclusive, optionally between 0.1 and 0.5 mm, inclusive.

In general, any material with a high thermal conductivity, such as greater than 10 W/m-K, greater than 45 W/m-K, greater than 65 W/m-K, or greater than 100 W/m-K, can be used to form the heat spreader layer. Optionally, the high thermal conductivity is at least about 10 W/m-K and not greater than about 400 W/m-K. Preferably, the heat spreader layer has a higher metal fraction than the flow distribution layer.

The heat spreader layer typically has a metal fraction of at least 5% volume and less than 60% volume, optionally the metal fraction is less than 30% volume or less than 20% volume, optionally the metal fraction is between 10% and 20% volume. In some forms, the metal in the heat spreader layer is in the form of fibers.

d. Quenching Layer i. Materials

Suitable materials for making the quenching layer 140 include, but are not limited to metals, metal alloys, or other heat conducting materials. Exemplary materials include, but are not limited to, metals, such as copper, silver, zinc, aluminum, nickel, platinum; alloys of these metals, and thermally conductive ceramics such as alumina, aluminum nitride, boron nitride, etc.

ii. Properties

Referring to FIG. 1A, the quenching layer 140 can be a thermally conductive layer that cools the reactant fluid and terminates free radical generated in the catalyst layer 110. In order to quench the reactant fluid efficiently, the quenching layer typically has a high thermal conductivity, e.g., about 10 W/m-K or greater and a high interstitial surface area. These properties enable the quenching layer to achieve fast heat transfer between the process channel(s) and the reactant fluid. In general, any material with a high thermal conductivity, such as greater than 10 W/m-K, greater than 45 W/m-K, greater than 65 W/m-K, or greater than 100 W/m-K, can be used to form the quenching layer. Optionally, the high thermal conductivity is at least about 10 W/m-K and not greater than about 400 W/m-K.

For terminating free radicals, the quenching layer typically has high interstitial surface area, such as for example 40-130 $cm^2/mL$, 50-130 $cm^2/mL$, 60-130 $cm^2/mL$, 70-130 $cm^2/mL$, 80-130 $cm^2/mL$, 90-130 $cm^2/mL$, 100-130 $cm^2/mL$, 40-670 $cm^2/mL$, 50-670 $cm^2/mL$, 40-200 $cm^2/mL$, 40-300 $cm^2/mL$, or 40-400 $cm^2/mL$. Optionally the interstitial surface area can be even greater, such as up to 6000 $cm^2/mL$, up to 5500 $cm^2/mL$, up to 2000 $cm^2/mL$, up to 1000 $cm^2/mL$, up to 680 $cm^2/mL$, or up to 500 $cm^2/mL$. The quenching layer 140 can be made of sintered metal mesh, non-sintered metal mesh, metal honeycomb, metal foam, perforated plate, or a combination thereof. In the quenching layer 140, the mesh structure is made of fibers, wools, or wires and typically has a metal fraction of at least 5% volume and less than 60% volume, optionally the metal fraction is less than 30% volume or less than 20% volume, optionally the metal fraction is between 10% and 20% volume. Preferably, the quenching layer 140 absorbs heat from the catalyst layer 110 and dissipates the heat away at a much lower temperature. The pore size of a material in this first layer can be of a dimension that balances free radical generation and propagation rate compared to free radical and flame extinction rate.

Suitable thicknesses for the quenching layer 140 include a thickness in a range from 0.1 mm to 20 mm, from 0.1 mm to 10 mm, from 0.1 mm to 1 mm, from 0.1 to 8 mm, or from 1 to 5 mm.

e. Flame Blocking Layer i. Materials

Similar to the quenching layer 140, suitable materials for making the flame blocking layer 150 include metals, metal alloys, and other heat conducting materials. Exemplary materials include metals, such as copper, silver, zinc, aluminum, nickel, platinum, and alloys of these metals.

ii. Properties

The flame blocking layer 150 is made of one or more porous materials with uniform opening size and high solid fraction so that the reactant fluid passes through this layer at a velocity higher than the flame speed. The flame speed is the measured rate of expansion of the flame front in a combustion reaction at given conditions. Therefore, even flame generated downstream of this layer will not propagate upstream.

Similar to the quenching layer 140, the flame blocking layer 150 can be made of sintered metal mesh, metal honeycomb, metal foam, perforated plate, or a combination thereof. The flame blocking layer 150 can have a metal fiber occupancy of between 5% volume and 60% volume, inclusive, preferably between 10% volume and 50% volume, inclusive, or between 20% volume and 30% volume, inclusive. Similarly the flame blocking layer 150 can have a porosity of between 40% volume and 95% volume, inclusive, preferably between 50% volume and 90% volume, inclusive, or between 70% volume and 80% volume, inclusive. In some forms, the flame blocking layer contains a higher metal fraction than the metal fraction of the quenching layer.

In some forms, the flame blocking layer 150 typically has a thickness between 0.1 mm and 5 mm, inclusive, between 0.1 mm and 2.5 mm, inclusive, or between 0.1 mm and 1 mm, inclusive.

In some forms, the flame blocking layer 150 can be a mesh structure made of fine fibers with diameters no greater than 6 microns. The fine fibers can be formed using any of the materials described above for forming the flame blocking layer 150. In some forms, the fine fibers can have a diameter between 0.1 micron and 6 microns, inclusive. In some forms, the flame blocking layer 150 can have a metal fraction between 5% volume and 60% volume, inclusive. The opening size of this layer can be less than 1 micron.

The quenching layer 140 and flame blocking layer 150 can collect the heat from the reactive fluid stream and transfer the heat to the reactor wall where it is removed. The thermal conductivity of the mesh in the quenching layer is at least 1 W/m-K and its effective thermal conductivity in the presence of gas flow is more than 10 W/m-K, preferably at least 45 W/m-K.

In some forms, the quenching layer 140 and the flame blocking layer 150 can be sintered together to form a flame arrestor. When sintered together, preferably, the quenching layer 140 and flame blocking layer 150 are made of the same material, typically one or more metals and/or metal alloys. Suitable materials include copper, brass, nickel, stainless steel, iron-aluminum-chromium (FeCrAl) alloy, etc.

In some forms, the barrier layer 120, the quenching layer 140, and the flame blocking layer 150 are sintered together.

Preferably, sintering of these layers occurs when the barrier layer 120 is made of a metal or a metal alloy.

In some forms, the catalyst layer 110, barrier layer 120, quenching layer 140, and flame blocking layer 150 are sintered together. Preferably, all of these layers are sintered together if the quenching layer 140 has an enhanced thermally conductive structure made of metal fibers, metal meshes, metal foams, metal alloy fibers, metal alloy meshes, or metal alloy foams.

In general, the flame blocking layer 150 effectively collects heat from the reaction fluid through its very fine microfibers and dissipates the heat to the quenching layer 140 which has a high thermal conductivity. Therefore, the combination of the quenching layer 140 and the flame blocking layer 150 can avoid flame formation and keep flames from propagating to the catalyst layer.

f. Support Structure

Referring to FIG. 1B, in some forms, the process channel contains a stack 1000' containing a plurality of composite catalyst structures and a mechanical supportive structure 160 to support the composite catalyst structures in the stack.

The mechanical supportive structure can be located in any suitable location that allows it to support the composite catalyst structures. Typically the mechanical supportive structure is aligned with the center of the reactor.

Generally each of the composite catalyst structures in the stack surrounds the mechanical support structure, such that the mechanical support structure 160 aids in maintaining the structure and location of the layers in the stack and alignment of the stack within the process channel. Optionally, the mechanical support structure contains one or more openings along its side walls and is open at the top and the bottom and hollow in the center of the mechanical support structure. This allows extra oxygen to be supplied along the length of the stack.

i. Materials

The mechanical supportive structure can be made from any material that can withstand the temperature and pressure conditions of the process channel. Suitable materials include metals and metal alloys.

ii. Properties

The mechanical supportive structure can be a solid rod, or a hollow tube to allow gas addition, or other suitable structure to provide static mixing or heat transfer. In some forms, the hollow tube contains perforations. The mechanical supportive structure can also include plates to hold the composite catalyst structures at specific volume fraction.

g. Flow Distribution Layer

Referring to FIG. 2A, optionally, the reactor includes a flow distribution layer 170 that initially contacts the reactant fluid i.e., inlet fluid containing organic compounds and oxygen, before it reaches the catalyst layer. The flow distribution layer can be adjacent to and stacked on the top of the catalyst layer. Preferably, the flow distribution layer does not contain a catalyst. The flow distribution layer is highly porous, and can have a porosity such as between 75% and 98%, inclusive, i.e., a total solid fraction between 25% and 2% volume, inclusive; between 85% and 98%, inclusive, i.e., a total solid fraction between 15% and 2% volume, inclusive; or between about 90% and 95%, i.e., the total solid fraction of this layer can be between 10% volume and 5% volume, inclusive.

i. Materials

Compared to the heat spreader layer, the materials used to form the flow distribution layer can have a variety of thermal conductivities; a high thermal conductivity is not required. Materials that can be included in the flow distribution layer include, but are not limited to, insulators, ceramics, metals, and metal alloys.

ii. Properties

The flow distribution layer 170 can generate uniform composition profiles, uniform temperature profiles, or uniform velocity profiles, or a combination thereof, before the reactant fluid reaches the catalyst layer. For instance, the flow distribution layer can provide resistance to flow, thereby converting the parabolic flow of a reactant fluid to plug flow before the reactant fluid contacts the catalyst layer.

Flow distributors used in industry are commonly made of metal mesh, metal foam, screen, or a perforated plate. For the process channel described herein, the flow distribution layer is typically made of sintered microfibrous media due to its isotropic physical properties such as thermal conductivities, and permeability for the given oxygen feeding scenarios as shown in FIGS. 2A, 2B, and 2C. Preferably, these uniform profiles are generated before a chemical reaction, such as an exothermic chemical reaction, occurs in the presence of oxygen, when the reactant fluid contacts the catalyst layer.

The structure of the flow distribution layer can be a mesh structure, such as a metal mesh containing micro-sized metal fibers, i.e., microfibrous medium, metal honeycomb, or metal monolith.

Preferably, the flow distribution layer contains metal fibers. In some forms, the diameter of the metal fibers can be between 0.5 micron and 50 microns, inclusive, between 1.5 microns and 32 micron, inclusive, preferably between 6 microns and 12 microns, inclusive. In some forms, the flow distribution layer has a metal fraction between 0.5% volume and 30% volume, inclusive, preferably between 1% volume and 15% volume.

In some forms, the effective thermal conductivity of a material within the flow distribution layer can be between 0.5 W/m-K and 75 W/m-K, inclusive, between 0.5 W/m-K and 50 W/m-K, inclusive, between 1 W/m-K and 45 W/m-K, inclusive, or between 1 W/m-K and 10 W/m-K, inclusive.

In some forms, the flow distribution layer has a thickness between 1 mm and 50 mm, inclusive, preferably between 5 mm and 30 mm, inclusive, most preferably between 10 mm and 20 mm.

III. Methods for Using the Reactors

The reactors can be used in a wide range of exothermic reactions, preferably partial oxidative reactions, most preferably catalytic partial oxidation reactions. Examples of catalytic partial oxidative reactions include, but are not limited to, alkene epoxidation, such as ethylene and propylene epoxidation; ammoxidation, such as the production of nitriles from the oxidation of alkenes in the presence of ammonia and oxygen; oxidative dehydrogenation, such as the removal of hydrogen from an organic compound in the presence of oxygen; oxidative coupling reactions, such as oxidative coupling of methane in the presence of oxygen to form ethane; and partial oxidation of methane to syngas.

Partial oxidation reactions are important in the current industrial production of various chemicals as well as the potential future production of other chemicals and fuels. Non-limiting examples of processes that involve partial oxidation reactions are described below.

1. Ethylene and Propylene Epoxidation

Ethylene and propylene epoxidation reactions are typically carried out through direct oxidation in an oxygen-lean environment, as described in Equations 1 and 2, below. The catalyst for the ethylene epoxidation reaction is metallic silver supported on various matrices, such as pumice, silica gel, various silicates and aluminosilicates, alumina, and silicon carbide. The catalyst can be further activated by some additives including antimony, bismuth, barium peroxide, etc. The optimal ethylene epoxidation process temperature is between 220° C. and 280° C., inclusive. The catalyst has low activity at lower temperatures and low selectivity at higher temperatures. Elevated pressures of between 1 and 3 MPa increase the productivity of the catalyst and facilitate absorption of ethylene oxide from the reacting gases. However, the current practice is to dilute ethylene concentration in the reaction stream to 10-12% volume and oxygen to 3% volume for safe operations, which leads severe product-reactant separation burdens and low volumetric production rate.

Propylene oxide is commonly produced by two general approaches: one involving hydrochlorination and the other involving oxidation by peroxides.

Silver based catalysts can also be used for propylene epoxidation. Alternatively, other catalysts can be used. The epoxidation of generic olefins is described by Eq. 3.

$$C_2H_4 + 1/2 O_2 \rightarrow C_2H_4O \ (\Delta H = -106 \text{ kJ/mol}) \quad \text{Eq. 1.}$$

$$C_3H_6 + 1/2 O_2 \rightarrow C_3H_6O \ (\Delta H = -114 \text{ kJ/mol}) \quad \text{Eq. 2.}$$

$$R-CH=CH-R' + 1/2 O_2 \longrightarrow R-\underset{\underset{O}{\diagdown \diagup}}{CH-CH}-R'. \quad \text{Eq. 3}$$

The enthalpies of these reactions are −106 kJ/mol and −114 kJ/mol. If the process runs adiabatically, the gas temperature rises can be as high as 1840° C. and 1660° C. If there are hot spots, some fraction of ethylene and propylene will go through complete oxidation (combustion) reactions as shown in Equations 4 and 5, which can cause severe disasters, such as explosions and/or fire propagation.

$$C_2H_4 + 3O_2 \rightarrow 2CO_2 + 2H_2O \ (\Delta H = -1,323 \text{ kJ/mol}) \quad \text{Eq. 4}$$

$$C_3H_6 + 3O_2 \rightarrow 3CO_2 + 3H_2O \ (\Delta H = -1,930 \text{ kJ/mol}) \quad \text{Eq. 5}$$

2. Ammoxidation

Ammoxidation is a chemical process to produce nitriles by oxidizing alkenes in the presence of ammonia and oxygen. It is sometimes called the SOHIO process. This process can be used to produce acrylonitrile:

$$CH_3CH=CH_2 + 3/2 O_2 + NH_3 \rightarrow NCCH=CH_2 + 3H_2O \ (\Delta H = -515 \text{ kJ/mol}) \quad \text{Eq. 6.}$$

Propylene ammoxidation is a strong exothermic reaction. The heat of reaction is −515 kJ/mol, and the corresponding adiabatic temperature rise is 3810° C.

In the SOHIO process, reactants propylene, ammonia, and air (oxidizer) are passed through a fluidized bed reactor containing the catalyst at a temperature between 400° C. and 510° C., inclusive, and pressure between 50 kPa and 200 kPa, inclusive. At such a high temperature rise and in the presence of oxygen, the process has a strong potential to experience thermal run away. As a result, it uses air as the oxygen source, i.e., a lower amount of oxygen, which limits the production capacity of the plant. The reactants pass through the reactor only once, then are quenched in aqueous sulfuric acid. Excess propylene, carbon monoxide, carbon dioxide, and nitrogen that do not dissolve are vented directly to the atmosphere or incinerated. Acrylonitrile, acetonitrile, hydrocyanic acid, and ammonium sulfate (from excess ammonia) remain in the aqueous solution. After bulk water is removed, acrylonitrile and acetonitrile are separated by distillation. Acetonitrile and hydrogen cyanide are significant byproducts that are recovered for sale. Historically, one of the first successful catalysts was bismuth phosphomolybdate supported on silica as a heterogeneous catalyst.

3. Oxidative Dehydrogenation (ODH)

Oxidative Dehydrogenation (ODH) is a chemical reaction that involves the removal of hydrogen from an organic molecule in the presence of oxygen, which as a hydrogen acceptor produces water. It has been widely employed to produce olefins and ketones from paraffins and alcohols.

For example, formaldehyde is produced industrially by catalytically oxidizing methanol. Methanol oxidation can also be viewed as a dehydrogenation using $O_2$ as the acceptor. The most common catalysts are silver metal or a mixture of iron and molybdenum or vanadium oxides. In the commonly used formox process, methanol and oxygen react at a temperature between about 250° C. and 400° C. in the presence of iron oxide in combination with molybdenum and/or vanadium to produce formaldehyde (Eq. 7).

$$CH_3OH + 1/2 O_2 \rightarrow CH_2O + H_2O \ (\Delta H = -148 \text{ kJ/mol}) \quad \text{Eq. 7.}$$

Another example is catalytic ODH of n-butane to produce butylene (Eq. 8). A common ODH catalyst for n-butane is based on vanadium oxides and molybdenum oxides on various supports such as MgO, SBA-SiO$_2$, and ZSM zeolites. The reaction is commonly carried out at a temperature in the range of 200-600° C. Various catalysts for butane ODH have been established using iron and chromium but have not achieved comparable results.

$$C_4H_{10} + 1/2 O_2 \rightarrow C_4H_8 + H_2O \ (\Delta H = -116 \text{ kJ/mol}) \quad \text{Eq. 8.}$$

Both methanol and butane ODH reactions are exothermic with adiabatic temperature rises of 1940 and 1040° C., respectively.

4. Oxidative Coupling Reactions (OCM)

Oxidative coupling of methane (OCM) oxidizes methane in the presence of $O_2$ over a catalyst at elevated temperatures to form ethane ($C_2H_6$) as a primary product (Eq. 9) and ethylene ($C_2H_4$) as a secondary product (Eq. 10). Because of the extremely high stability of $CH_4$ (C—H bond energy is 435 kJ/mol), the OCM reaction has to be carried out at high temperatures (750-950° C.).

During the OCM process, the methyl free radicals are formed and coupled in the gas phase to form ethane and the hydrogen radical forms water in the presence of oxygen, which makes the overall OCM reaction exothermic. Ethane can further form ethylene through a dehydrogenation reaction. Methyl radicals also react with oxygen to form CO and $CO_2$, which are the undesired products. Both reactions are highly exothermic and have adiabatic temperature rises of 3490° C. and 4300° C., respectively. Temperature gradients as high as 150-300° C. within a catalyst bed are common. To keep the OCM from thermal run-away, the OCM reaction is carried out in an oxygen lean environment with the single pass $CH_4$ conversion limited at 20-30% and the selectivity to $C_2$ (i.e. $C_2H_6$ and $C_2H_4$) up to 80%, which limits the single pass $C_2$ yield to about 25%.

$$2CH_4 + 1/2 O_2 \rightarrow C_2H_6 + H_2O \ (\Delta H = -175 \text{ kJ/mol}) \quad \text{Eq. 9.}$$

$$2CH_4 + O_2 \rightarrow C_2H_4 + 2H_2O \ (\Delta H = -175 \text{ kJ/mol}) \quad \text{Eq. 10.}$$

As noted above, all of these catalytic reactions are highly exothermic and have significant adiabatic temperature rises. Additionally, the selectivity of these reactions is sensitive to temperature such that reactors undergoing excessive reaction could develop hot spots that lead to reactant ignition and/or a product selectivity that shifts toward total oxidation. However, each of these reactions can be conducted using one or more of the reactors described herein in a safer and more efficient manner than previously achieved. In particular, the formation of hot spots is generally avoided using the reactors described herein.

To address these competing influences, and the poor thermal conductivity that exists in packed bed reactors, most industrial practitioners have employed one or more of the following measures, including: (i) small diameter reactor tubes with high surface to volume ratios for higher heat transfer rates, (ii) reduce the reaction rate per unit volume inside tubular reactors, by placing inert materials into catalyst beds, (iii) sub-stoichiometric levels of oxygen to limit the extent of reaction, (iv) inert gases added to the reactant fluid to serve as a thermal sink for the exothermicity of the reaction, and (v) introduce inert gases to dilute combustible gas concentration to below the explosion threshold. All the above noted steps are undertaken to lower the rate of reaction per unit volume so that the heat generated by the reaction inside the tubular packed bed reactor is equal to the heat removed from the external surface of the tubular reactor wall and thus the temperature inside the reactor tube can be controlled in a robust fashion within a desired range.

The disadvantages of the above noted approaches are numerous. Small diameter tubes and those diluted with inerts often yield large, complex and costly reactor systems with hundreds of thousands of individual tubes (ca. 1" in diameter and often 20 ft long) in order to provide sufficient external surface area for adequate heat transfer. Using sub-stoichiometric levels of oxygen means that low per pass conversion is obtained resulting in costly downstream separation and reactant recycle needs. Also, reduced oxygen levels may be necessitated by safety concerns and a requirement to keep all reactant composition levels below the LEL. Finally, diluting the reactant stream with inert gases as a heat sink material also serves to increase vessel size with a concomitant increase in costly downstream separation and recycle.

The reactors described herein are able to overcome the above noted deficiencies. The process channel containing a micro-structured catalyst carrier or support that has exceedingly high thermal conductivity to the inside wall of the process channel, reduces undesired intrabed hot spots that lead to reactant ignition and poor selectivity to partial oxidation products. High thermal conduction further allows non-diluted and more active catalysts to be used in larger process channels, about 4-inch channels for highly exothermic reactions. For example, when the process channel is a tube, this approach permits much smaller and lower cost reactors to be used, which employ a greatly reduced number of larger diameter and shorter tubes. The micro-structured catalyst carrier or support has small much higher interstitial surface area due to the use of micron-sized fibers (ca. 1 to 100 micron), so that any free radicals produced are unable to propagate a flame or explosion, because they are rapidly quenched by wall collisions. This measure permits higher levels of oxygen to be used (i.e., levels above the LEL), which increases both volumetric reactivity and conversion per pass resulting in reduced separation and reactant recycle costs. The combination of the above influences can dramatically affect the capital expenditure and operating expenses for performing exothermic reactions, particularly partial oxidation reactions.

The reactors described herein also provide a higher level of process safety, and reduce the energy required/consumed to produce the products by making the process more efficient due to the reduced requirement for separation and recycle. This gain in energy efficiency per pound of product produced also provides a sizable reduction in global greenhouse gas emissions due to the very large scale and utilization of some of the above noted chemicals.

Moreover, the aforementioned reactions are highly exothermic and involve high temperature operations in the presence of oxygen and combustible gases such as $CH_4$, $C_2H_6$, $C_2H_4$, etc. These gas mixtures can generate intrabed hot spots which deleteriously affect catalytic selectivity, reactant ignition to total oxidation products, or flames and free radical combustion inside the bed if the mixture is between the LEL (i.e., lower explosive limit) and UEL (i.e., upper explosive limit). The LEL and UEL for reactants and thresholds for oxygen depends on the particular process, and can be ascertained for each process. These undesirable effects can be enhanced in the presence of mal-mixing or gas channeling within the bed. These effects drive the inherent safety need to operate the catalytic reactor and process in a deliberately inefficient manner below the LEL. Therefore, there are both safety and operational opportunities to develop and use structured catalyst materials that can function as both catalyst carriers and flame arrestors. The degree to which such structures can also enhance heat transfer to the interior wall of the process channel (i.e., thermal conduction) and mass transport within the catalyst layer or inside the catalyst particle itself will further enhance the efficacy of the reactor as well.

Conventional flame arrestors are typically made of metal foams, wire meshes or sheet screens. They capture the heat from a flame front traveling at sub-sonic velocities, and decrease the temperature of the burning gas/air mixture below its auto-ignition temperature. If they possess small and tortuous pore structures they can also enhance the rate of free radical decay by virtue of wall collisions. As a result, flames cannot propagate through the flame arrestor. In order to make the flame arrestor work, enough arrestor depth in the form of heat capacity of wall collisions is required to keep the flame from forming and/or propagating.

Because of the exothermicity of these reactions, hot spots can originate anywhere in the catalyst layer and ignite the other reactants within the reactor. Therefore, there is a need to prevent the flame generation and propagation and also carry out the heterogeneous catalytic reactions at elevated temperatures. It might be possible to have the catalytic layer in several sections divided by flame arrestors. However, this arrangement still cannot solve the flame generation in the individual catalytic layer sections, if the length of the catalytic layers, e.g., OCM catalytic layers are not short enough. Moreover, the cost of such a series of OCM reaction and flame arrestor combinations can be very high, which makes it of no applicable interests. In the proposed approach, instead of using a series of bulky standalone flame arrestors, micro-scale flame arrestors are integrated with a catalyst layer during reactor preparation.

Oxygen can be added by mixing oxygen and a reactant fluid containing organic compounds prior to the reactant fluid contacting the catalytic layer. In most cases, oxygen is added only at low levels so that the organic gas is above the UEL (upper explosive limit), which is widely adopted and practiced in industry (FIG. 2A). However, this will also generate low single-pass conversion as mentioned before. In order to boost the single-pass conversion, extra oxygen can be further added along the reactor axis so that all local organic content is above the UEL level though the accumulated oxygen level is high enough to achieve significant single-pass conversion. Extra oxygen can be added from the side of the reactor (FIG. 2B) or from within the supportive structure itself (FIG. 2C). In both cases, an extra distribution layer is required for each oxygen entry. For extra safety measures, oxygen can be added with diluents such as nitrogen, argon, or even the organic reactant(s) of the desired reaction, although diluents are undesirable unless absolutely required to suppress temperature rises.

IV. Methods of Making

The process channels described above can be constructed using any material that provides sufficient strength, dimensional stability and heat transfer characteristics for carrying out the exothermic reactions described herein. Examples of suitable materials include steel (e.g., stainless steel, carbon steel, etc), aluminum, titanium, nickel, and alloys of any of the foregoing metals, plastics (e.g., epoxy resins, UV cured resins, thermosetting resins, etc), monel, inconel, ceramics, glass, composites, quartz, silicon, or a combination of two or more thereof. The process channel can be fabricated using techniques known in the art, including but not limited to, wire electrodischarge machining, conventional machining, laser cutting, photochemical machining, electrochemical machining, molding, water jet, stamping, etching (for example, chemical, photochemical or plasma etching) and combinations thereof. The composite catalyst structures may be constructed by forming layers or sheets that allow fluid flow through the structures. A stack of layers can be assembled via diffusion bonding, laser welding, diffusion brazing, and similar methods to form an integrated structure, such as the composite catalyst structure or the process channel. The reactor as a whole has appropriate manifolds, valves, conduit lines, etc. to control flow of the reactant fluid and product. These are not shown in the drawings, but can be readily provided by those skilled in the art.

The numerical ranges disclosed herein disclose individually each possible number in such a range, as well as any sub-ranges and combinations of sub-ranges encompassed therein. For example, a diameter range (between 0.5 micron and 50 microns, inclusive) is intended to disclose individually every possible numerical value and/or sub-range encompassed within. For example, a diameter range of between 1 micron and 10 micron discloses 1 micron, 2 microns, 3 microns, 4 microns, 5 microns, 6 microns, 7 microns, 8 microns, 9 microns, and 10 microns, as well as discloses sub-ranges encompassed within, such as between 2 microns and 9 microns, inclusive, between 3 microns and 8 microns, inclusive, between 1 micron and 5 microns, inclusive, etc. Further, a concentration range or volume percent range, such as between 1% and 2% by volume of a area discloses, the individual values and fractions thereof, such as 1%, 1.1%, 1.2%, 1.32%, 1.48% etc. , as well as sub-ranges encompassed within.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A reactor suitable for conducting a partial oxidative reaction, wherein the reactor comprises a vessel comprising a process channel and two or more composite catalyst structures in the form of a stack,
   wherein each composite catalyst structure comprises a catalyst layer, wherein the catalyst layer comprises a porous substrate and a catalyst,
   wherein the porous substrate comprises sintered microfibrous media comprising a metal or metal alloy, non-sintered metal mesh, sintered metal mesh, metal honeycomb, metal monolith, ceramics, or a combination thereof,
   wherein at least a portion of at least one of the two or more composite catalyst structures comprises a layer comprising a porous heat transfer structure configured to quench free radicals and prevent explosions or propagation of a fire during the partial oxidative reaction, and
   wherein the porous heat transfer structure comprises a heat spreader layer that does not contain the catalyst.

2. The reactor of claim 1, further comprising a flow distribution layer on top of at least one of the two or more composite catalyst structures, wherein the vessel further comprises an inlet, and wherein the inlet is located above the flow distribution layer.

3. The reactor of claim 1, wherein at least one of the two or more composite catalyst structures further comprises a barrier layer configured to prevent the catalyst from migrating out of the catalyst layer.

4. The reactor of claim 1, wherein the heat spreader layer has a thermal conductivity of at at least 10 W/m-K.

5. The reactor of claim 4, wherein the heat spreader layer contains two layers, where the first layer is a flame blocking layer that contains a higher metal fraction than the metal fraction of the second layer, wherein the second layer is a quenching layer.

6. The reactor of claim 5, wherein the flame blocking layer and the quenching layer contain the same metal or metal alloy, and wherein the flame blocking layer and the quenching layer are sintered to each other.

7. The reactor of claim 4, wherein the heat spreader layer comprises a material selected from the group consisting of a metal screen, metal mesh, metal foam, perforated plate, and microfibrous media.

8. The reactor of claim 1, wherein the porous substrate in the catalyst layer is sintered microfibrous media comprising a metal or metal alloy.

9. The reactor of claim 1, wherein the amount of catalyst in the catalyst layer ranges from about 1 to about 25 vol %.

10. The reactor of claim 1, wherein the catalyst is in the form of catalyst particles and the catalyst particles are dispersed in the substrate.

11. The reactor of claim 10, wherein at least one of the two or more composite catalyst structures further comprises a barrier layer, wherein the barrier layer is located beneath the catalyst layer, and wherein the barrier layer has a pore size that is smaller than the size of catalyst particles.

12. The reactor of claim 11, wherein the barrier layer comprises a mesh structure, metal microfibrous media, or ceramic microfibrous media.

13. The reactor of claim 11, wherein each of the barrier layer and the heat spreader layer is formed from a metal or metal alloy, and wherein the heat spreader layer and barrier layer are sintered to each other.

14. The reactor of claim 1, wherein the two or more composite catalyst structures are the same or different.

15. The reactor of claim 14, wherein the vessel further comprises a mechanical supportive structure, and wherein each of the composite catalyst structures is on or surrounds the mechanical supportive structure.

16. The reactor of claim 15, wherein the vessel further comprises a reactant fluid inlet and a product fluid outlet.

17. The reactor of claim 16, further comprising an oxygen inlet.

18. A reactor suitable for conducting a partial oxidative reaction, wherein the reactor comprises a vessel comprising two or more composite catalyst structures in the form of a stack, wherein at least one of the two or more composite catalyst structures comprises:
 (i) a catalyst layer comprising
  (a) a catalyst, and
  (b) sintered microfibrous media, non-sintered metal mesh, sintered metal mesh, metal honeycomb, porous metal monolith, ceramics, or a combination thereof, and
 (ii) a barrier layer comprising a material with pores or interstitial spaces of a sufficient size to prevent the catalyst from migrating out of the catalyst layer, or
 (iii) a heat spreader layer configured to dissipate heat, or
 (iv) both (ii) and (iii),
 wherein the barrier layer, the heat spreader layer, or both, comprise a metal or metal alloy, and wherein the catalyst is not present in the heat spreader layer.

19. A method for conducting a partial oxidative reaction, comprising flowing a reactant fluid through the reactor of claim 1.

20. The method of claim 19, wherein the reactant fluid comprises organic compounds and oxygen.

21. The method of claim 19, wherein the reactor operates at a temperature ranging from 200° C. to 950° C.

22. The method of claim 19, wherein the amount of oxygen that can safely be fed to the reactor without causing a fire or explosion is greater than the lower explosion limit (LEL) for the partial oxidative reaction.

23. The reactor of claim 1, wherein the catalyst layer conducts heat.

24. The reactor of claim 1, wherein the substrate is a sintered metal.

25. The reactor of claim 1, wherein the two or more composite catalyst structures in the stack are oriented perpendicularly to a direction of flow of a reactant fluid in the process channel, when the reactant fluid flows axially along the process channel.

* * * * *